(12) United States Patent
Uckun et al.

(10) Patent No.: US 6,960,606 B2
(45) Date of Patent: Nov. 1, 2005

(54) ADAMANTYL THIAZOLE THIOUREAS

(75) Inventors: Faith M. Uckun, White Bear Lake, MN (US); Taracad K. Venkatachalam, Maplewood, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 10/420,031

(22) Filed: Apr. 15, 2003

(65) Prior Publication Data

US 2003/0207921 A1 Nov. 6, 2003

Related U.S. Application Data

(63) Continuation of application No. PCT/US00/41290, filed on Oct. 19, 2000.

(51) Int. Cl.⁷ .................... A61K 31/425; C07D 277/20
(52) U.S. Cl. ........................................ 514/371; 548/196
(58) Field of Search ........................... 548/196; 514/371

(56) References Cited

U.S. PATENT DOCUMENTS 5,593,993 A * 1/1997 Morin et al. ................ 514/247
5,998,411 A  12/1999 Vig et al.

FOREIGN PATENT DOCUMENTS

WO  WO 99/47501  9/1999
WO  WO 00/21565  4/2000

OTHER PUBLICATIONS

Bell, J Med Chem 38 4929, 1995.*
Ahgren, et al., *Antimicro. Agents Chemother*, 1995, 39(6), 1329–35 The PETT Series, a New Class of Potent Non-nucleoside Inhibitors of Human Immunodeficiency Virus Type 1 Reverse Transcriptase.

Bell, et al.,*J. Med. Chem.*, 1995, 38(25), 4929–36 Phenethylthiazolethiourea (PETT) Compounds a New Class of HIV–1 Reverse Transcriptase Inhibitors. 1. synthesis and Basic Structure–Activity Relationship Studies of PETT Analogs.

Bosworth et al., *Nature*, 1989,341:167–168 Scintillation Proximity Assay.

Cantrell et al.,*J. Med. Chem.*, 1995,39(21), 4261–4274 Phenethylthiazolylthiourea (PETT) Compounds as a New Class of HIV–1 Reverse Transcriptase Inhibitors. 2. Synthesis and Further Structure–Activity Relationship Studies of PETT Analogs.

Hogberg et al., *Bioorg. Med. Chem. Lett.*, 2000, 10(3), 265–268 Bioisosteric Modification of PETT–HIV–1 RT–Inhibitors: Synthesis and Biological Evaluation.

Kohlstaedt, et al., *Science*, 1992, 256, 1783–1790 Crystal Structure at 3.5 A Resolution of HIV–1 Reverse Transcriptase Complexed with an Inhibitor.

Uckun et al., 1998, *Antimicrobial Agents and Chemotherapy*, 42:383 TXU (Anti–CD7)–Pokeweed Antiviral Protein as a Potent Inhibitor of Human Immunodeficiency Virus.

* cited by examiner

*Primary Examiner*—Kamal Saeed
(74) *Attorney, Agent, or Firm*—Merchant & Gould P.C.

(57) ABSTRACT

Novel aromatic and heterocyclic thiazolyl thiourea compounds, pharameutical compositions including such, and methods for their use are disclosed. The compounds are effective agents for the treatment of HIV infection, including non-nucleoside inhibitor-resistant, and multi-drug resistant strains of HIV.

7 Claims, 4 Drawing Sheets

ADAMANTYL THIAZOLE THIOUREAS

FIELD OF THE INVENTION

The invention relates to inhibitors of reverse transcriptase effective against HIV, including mutant strains of HIV, and effective in the treatment of NNI-resistant and multi-drug resistant HIV infection.

BACKGROUND OF THE INVENTION

Agents currently used to treat HIV infection attempt to block replication of the HIV virus by blocking HIV reverse transcriptase or by blocking HIV protease. Three categories of anti-retroviral agents in clinical use are nucleoside analogs (such as AZT), protease inhibitors (such as nelfinavir), and the recently introduced non-nucleoside reverse transcriptase inhibitors (NNRTI), such as nevirapine, delavirdine and efavirenz.

The recent development of potent combination anti-retroviral regimens has significantly improved prognosis for persons with HIV and AIDS. Combination therapies may be a significant factor in the dramatic decrease in deaths from AIDS (a decrease in death rate as well as absolute number). The most commonly used combinations include two nucleoside analogs with or without a protease inhibitor.

NNRTI compounds such as nevirapine have been used in combination with AZT and/or protease inhibitors for the treatment of HIV. A new series of effective drug cocktails will most likely involve other NNRTIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) NNRTI targeting RT provide a very promising therapy to overcome the drug resistance problem. RT mutant strains resistant to such a triple action drug combination would most likely not be able to function.

Dozens of mutant strains have been characterized as resistant to NNTI compounds, including L1001, K103N, V106A, E138K, Y181C and Y188H. In particular, the Y181C and K103N mutants may be the most difficult to treat, because they are resistant to most of the NNRTI compounds that have been examined. Examples of NNRTI-resistant strains include A17, with a Y181C mutation, and A17 variant, with Y181C plus K103N mutations.

Novel NNRTI designs able to reduce RT inhibition to subnanomolar concentrations with improved robustness against the most commonly observed mutants and preferably able to inhibit the most troublesome mutants are urgently needed. New antiviral drugs will ideally have the following desired characteristics: (1) potent inhibition of RT; (2) minimum cytotoxicity; and (3) improved ability to inhibit known, drug-resistant strains of HIV. Currently, few anti-HIV agents possess all of these desired properties.

NNIs have been found to bind to a specific allosteric site of HIV-RT near the polymerase site and interfere with reverse transcription by altering either the conformation or mobility of RT, thereby leading to a noncompetitive inhibition of the enzyme (Kohlstaedt, L. A. et al., Science, 1992, 256, 1783–1790).

In a systematic search for derivatives of thiourea compounds as useful anti-AIDS drugs, several structurally distinct thiourea compounds have been identified as potent NNRTI of HIV-1 RT. A series of selected thazolyl thiourea derivatives targeting the NNI binding site of HIV reverse transcriptase (RT) were synthesized and tested for activity against wild-type and NNRTI-resistant HIV. Rational design and synthesis of these thazolyl thiourea derivatives was aided by biological assays and their anti-HIV activity. Some of these novel derivatives exhibited subnanomolar efficacy in the inhibition of HIV with minimal cytotoxicity. These compounds are useful in the treatment of HIV infection, and have particular efficacy against mutant strains, making them useful in the treatment of multi-drug resistant and NNRTI-resistant HIV.

The present invention provides the synthesis and methods for using novel aromatic/heterocyclic thiazolyl thiourea compounds based on anti-HIV activity.

SUMMARY OF THE INVENTION

The invention provides novel thiazolyl-thiourea compounds as newly identified non-nucleoside inhibitors (NNRTI) of HIV reverse transcriptase. The novel thiazolyl-thiourea compounds, compositions, and methods of the invention are useful in the treatment of HIV infection, with particular efficacy against multiple strains of HIV, including NNRTI-resistant and multi-drug resistant mutant strains.

The thiazolyl-thiourea compounds, compositions, and methods of the invention are useful for inhibiting reverse transcriptase activity and inhibiting replication of multiple strains of HIV, including NNRTI-resistant and multi-drug resistant strains. In particular, the thiazolyl-thiourea compounds of the invention are useful for treating retroviral infection in a subject, such as an HIV-1 infection, by administration of the thiazolyl-thiourea compounds of the invention, for example, in a pharmaceutical composition.

The compounds of the invention may be combined with carriers and/or agents to enhance delivery to sites of viral infection, such as targeting antibodies, cytokines, or ligands. The compounds may include chemical modifications to enhance entry into cells, or may be encapsulated in various known delivery systems.

In one embodiment of the present invention, the thiazolyl-thiourea compound has a structure shown in Formula I.

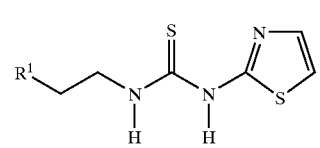

$R^1$ is an aryl, heteroaryl, cycloalkyl or aryloxy moiety which may be substituted or unsubstituted. Moreover, compounds Formula I may be in the form of a pharmaceutically acceptable salt.

In another embodiment of the present invention, the thiazolyl-thiourea compound has a structure shown in Formula II.

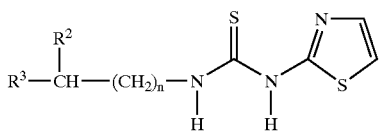

R² is hydrogen, halogen, alkyl or arylalkyl and n is 0 or 2. R³ is a substituted or unsubstituted, saturated or unsaturated, 5 or 6 member organic monocyclic ring having 0 to 3 heteroatoms selected from O, S, and N; or a substituted or unsubstituted, saturated or unsaturated, 7- to 10-member organic bicyclic or tricyclic ring having 0 to 3 heteroatoms selected from O, S, and N; or a pharmaceutically acceptable salt thereof.

The thiazolyl-thiourea compounds and compositions useful in the invention exhibit very low cytotoxicity and very high potency against HIV including both wild-type and NNRTI-resistant HIV.

Specific compounds and methods of the invention are described more fully in the Detailed Description and in the Examples below.

DETAILED DESCRIPTION OF THE INVENTION

Definitions

Figure 1A:
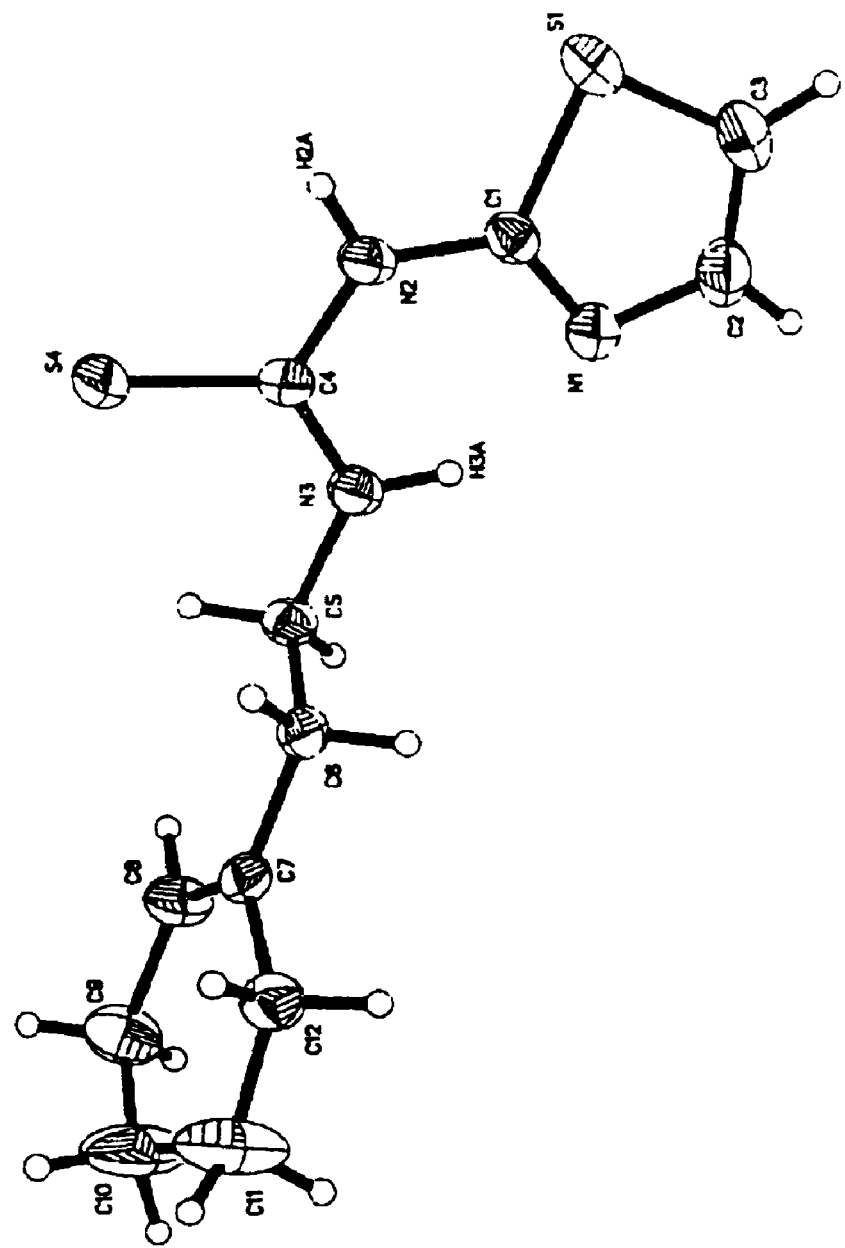
FIGS. 1A, 1B, 1C and 1D are schematic diagrams of X-ray crystal structures of Compound 2: N-[2-(1-Cyclohexenylethyl)]-N'-[2-(thiazolyl)]thiourea (FIG. 1A), Compound 6: N-[1-(1-Furoylmethyl)]-N'-[2-(thiazolyl)] thiourea (FIG. 1B), Compound 7: N-[3-(2-Imidazole) propyl]-N'-[2-(thiazolyl)]thiourea (FIG. 1C), and Compound 8: N-[2-(2-Indole)ethyl]-N'-[2-(thiazolyl)]thiourea (FIG. 1D).

When used herein, the following terms have the indicated meanings:

"Retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

"Reverse transcriptase (RT)" refers to an enzyme having reverse transcriptase activity and an NNI binding site similar to that of HIV-1 RT and to which ligands that bind the composite binding pocket of the invention bind.

"Reverse transcriptase (RT) activity" means the ability to effect reverse transcription of retroviral RNA to proviral DNA. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., Nature 1989, 341:167–168.

"NNRTI" means non-nucleoside reverse transcriptase inhibitor. In the context of the invention, non-nucleoside inhibitors of MV reverse transcriptase (RT) are defined.

"Mutant HIV" means a strain of HIV having one or more mutated or altered amino acids as compared with wild type.

The term "wild-type" as used herein, means the phenotype that is characteristic of most of the members of a species occurring naturally and contrasting wit the phenotype of a mutant.

"Multi-Drug Resistant HIV" means one or more HIV strain that is resistant to treatment with one or more chemotherapeutic agent.

"Therapeutically effective amount" is a dose that provides some therapeutic benefit on administration, including, in the context of the invention, reduced viral activity or viral load in a patient, and also including inhibition of viral RT activity and/or replication of virus.

"Docking" a compound in a binding pocket means positioning a model of a compound in a model of the binding pocket. In one embodiment, the docking is performed with the use of computer software, such as the Affinity program within InsightII (Molecular Simulations Inc., 1996, San Diego, Calif.). Docking permits the identification of positions of the compound within the binding pocket that are favored, for example, due to minimization of energy.

"Conjugate" means a complex formed with two or more compounds.

"Targeting moiety" means a compound that serves to deliver the compound of the invention to a specific site for the desired activity. Targeting moieties include, for example, molecules that specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

"Alkyl" refers to straight or branched hydrocarbon radicals, such as methyl, ethyl, propyl, butyl, octyl, isopropyl, tert-butyl, sec-pentyl, and the like. Alkyl groups can either be unsubstituted or substituted with one or more substituents, such as, for example, halogen, hydroxy, alkoxy, aryl, arylalkyl, aralkoxy, oxo and the like. Typically, alkyl groups include 1 to 8 carbon atoms, preferably 1 to 6, more preferably 1–4, and most preferably 1 to 3 carbon atoms.

"Cycloalkyl" refers to a 3- to 8-member hydrocarbon ring containing 0 to 3 heteroatoms selected from O, N, and S; or a bicyclic or tricyclic 4- to 12-member hydrocarbon ring system containing 0 to 3 heteroatoms selected from 0, N, and S. Cycloalkyl groups can either be unsubstituted or substituted with one or more substituents, such as, for example, halogen, hydroxyl, alkoxy, aryl, arylalkyl, aralkoxy, oxo and the like.

"Aryl" refers to monovalent unsaturated aromatic carbocyclic radicals having a single ring, such as phenyl, or multiple condensed rings, Such as naphthlyl or anthryl, which can be optionally substituted by substituents such as, for example, halogen, alkyl, alkoxy, hydroxy, and the like.

"Heteroaryl" refers to a heteroaromatic ring containing 1 to 3 heteroatoms selected from O, N, and S; a bicyclic 9- or 10-member heteroaromatic ring system containing 1 to 3 heteroatoms selected from O, N, and S; or a tricyclic 13- or 14-member heteroaromatic ring system containing 1 to 3 heteroatoms selected from O, N, and S; each of which rings can be optionally substituted by substituents such as halogen, alkyl, alkoxy, hydroxy, and the like.

"Aryloxy" refers to an oxygen atom substituted with an aryl radical as defined above. Typical aryloxy groups include phenoxy, naphthoxy and the like. Preferable aryloxy groups include phenoxy.

"Alkoxy" refers to an oxygen atom substituted with an alkyl radical as defined above. Typical alkoxy groups include methoxy, ethoxy, propoxy, isopropoxy, and the like. Preferable alkoxy groups include methoxy and ethoxy.

"Arylalkyl" refers to an alkyl radical defined as above substituted with an aryl radical as defined above. Typical arylalkyl groups include phenethyl, benzyl, and naphthethyl.

"Aralkoxy" refers to an alkoxy group as defined above where the alkyl group is substituted with an aryl radical as defined above.

"Halo" refers to fluoride, chloride, bromide, and iodide radicals.

Compounds of the Present Invention

Compounds of the present invention are thiazolyl-thiourea compounds useful as non-nucleoside inhibitors of RT having formula I.

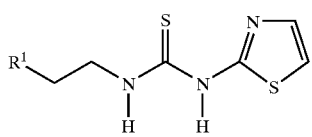

I

The $R^1$ moiety in compounds of formula I is typically substituted or unsubstituted aryl, heteroaryl, cycloalkyl, or aryloxy. For example, $R^1$ may be substituted or unsubstituted phenyl, phenoxy, indolyl, pyridyl, piperidinyl, and the like. Additionally, $R^1$ may be substituted at one or more positions with, for example, halo, $(C_1-C_4)$ alkyl, hydroxyl, and the like. Preferably, $R^1$ is substituted with methyl or hydroxyl.

Exemplary compounds of the invention are N-[2-(phenoxyethyl)]-N'-[2-(thiazolyl)]thiourea where $R^1$ is an unsubstituted phenoxy, N-[2-(2-indole)ethyl]-N'-[2-(thiazolyl)]thiourea where $R^1$ is an unsubstituted indolyl, N-[2-(2-piperdine)ethyl]-N'-[2-(thiazolyl)]thiourea where $R^1$ is an unsubstituted piperidinyl, and N-[2-pyridylethyl]-N'-[2-(thiazolyl)]thiourea where $R^1$ is an unsubstituted pyridyl.

In one preferred embodiment, $R^1$ is phenyl, optionally substituted with one or more substituents, for example, with halo, $(C_1-C_4)$ alkyl or hydroxy where the phenyl group is not monosubstituted with methyl or hydroxy at an ortho position. Exemplary compounds of the invention are N-[2-(4-methylphenyl)ethyl]-N'-[2-(thiazolyl)]thiourea (Compound 4) where $R^1$ is a phenyl substituted with methyl in the para position and N-[2-(4-hydroxyphenyl)ethyl]-N'-[2-(thiazolyl)]thiourea (Compound 10) where $R^1$ is a phenyl substituted with hydroxy in the para position.

In another embodiment of the present invention, the thiazolyl-thiourea compound has a structure shown in Formula II.

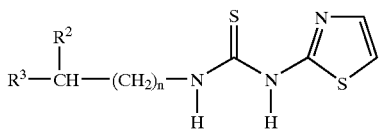

II

Values of n in compounds of formula II include 0, 1, 2, 3, and 4. Preferably, n is 0, 1, or 2. Most preferably, n is 0 or 2.

The $R^2$ moiety in compounds of formula II is typically hydrogen, halogen, alkyl or arylalkyl. Preferably, $R^2$ is hydrogen, $C_1-C_6$ alkyl or halogen. Most preferably, $R^2$ is methyl or ethyl.

The $R^3$ moiety in compounds of formula II is typically a substituted or unsubstituted, saturated or unsaturated, 5 or 6 member organic monocyclic ring having 0 to 3 heteroatoms selected from O, S, and N. Additionally, $R^3$ includes substituted or unsubstituted, saturated or unsaturated, 7- to 10-member organic bicyclic or tricyclic rings having 0 to 3 heteroatoms selected from O, S, and N. Substituents on $R^3$ include, for example, halogen, alkyl, and hydroxyl.

Preferably, $R^3$ is, for example, substituted or unsubstituted adamantyl, phenyl, furoyl, thiazolyl, cyclohexenyl, imidazolyl, indolyl, piperidinyl, pyridinyl, or 2-pyrrolidinonyl.

In one preferred embodiment of compounds of formula II, n is 0, $R^2$ is hydrogen or alkyl and $R^3$ is furoyl, adamantyl or phenyl. Exemplary compounds of the invention are N-[1-(1-adamantyl)methyl]-N'-[2-(thiazolyl)]thiourea (Compound 5) where W is unsubstituted adamantyl and $R^2$ is hydrogen, N-[1-(1-furoylmethyl)]-N'-[2-(thiazolyl)]thiourea where $R^3$ is unsubstituted furoyl and $R^2$ is hydrogen, and N-[(α-ethylbenzyl]-N'-[2-(thiazolyl)]thiourea (Compound 13) where $R^3$ is phenyl and $R^2$ is ethyl.

In another preferred embodiment of compounds of formula II, n is 2, $R^2$ is hydrogen and $R^3$ is imidazolyl, indolyl, piperidinyl or 2-pyrrolidinonyl. Exemplary compounds of the invention are N-[3-(2-imidazole)propyl]-N'-[2-(thiazolyl)]thiourea (Compound 7) where $R^3$ is unsubstituted imidazole, and N-[3-(pyrrolidinone)propyl]-N'-[2-(thiazolyl)]thiourea (Compound 12) where $R^3$ is unsubstituted imidazole.

The compounds of the invention preferably bind to a specific allosteric site of HIV-RT near the polymerase site and interfere with reverse transcription, for example, by altering either the conformation or mobility of RT.

The compounds of the invention may also be in the form of pharmaceutically acceptable acid addition salts. Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, asorbic, maleic, methanesulfonic, tetrafluoroboric, methanesulfonic, trifluoromethanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Methods of Using the Compounds of the Invention

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

The methods of the invention are useful for inhibiting reverse transcriptase and/or replication of multiple strains of HIV, including mutant strains such as multi-drug-resistant and NNRTI-resistant strains, and include treating a retroviral infection in a subject, such as an HIV-1 infection, by administering an effective inhibitory amount of a compound or a pharmaceutically acceptable acid addition salt of a compound of Formula I or II. The compound of Formula I or II is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The compounds of Formula I or II can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, and sterile injectable preparations, such as sterile injectable aqueous or oleagenous suspensions or suppositories. In one embodiment, the thiazolyl-thiourea compounds of the invention can be applied intravaginally and/or topically, for example in gel form, for prevention of heterosexual transmission of HIV.

For oral administration as a suspension, the compositions can be prepared according to techniques well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The compounds of formula I or II can be administered in combination with other agents useful in the treatment of HIV infection, AIDS or ARC. For example, the compound of the invention can be administered in combination with effective amounts of an antiviral, immunomodulator, anti-infective, or vaccine. The compound of the invention can be administered prior to, during, or after a period of actual or potential exposure to retrovirus, such as HIV.

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

Particularly useful targeting moieties for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting anti-viral treatments to target cells. Methods for producing conjugates of the compounds of the invention and the targeting moieties are known.

Methods of Making the Compounds of the Invention

The compounds of the invention may be prepared as shown in Scheme 1. In brief, a 2-aminothiazole (A) is contacted with a thiocarbonyldimidazole in an appropriate organic solvent such as, for example, acetonitrile or dimethylformamide under an inert atmosphere at ambient temperatures to form a thiazolethiocarbonylimidazole product (B). The resulting product (B) is then isolated using methods known to those of skill in the art. The product (B) is then further contacted with an appropriate amine in an appropriate organic solvent such as, for example, acetonitrile or dimethylformamide under an inert atmosphere. The resulting product (C) is then isolated using methods known to those of skill in the art. Compound (C) is further purified using silica gel column chromatography. The physicochemical properties of the compounds are determined using standard analytical methods.

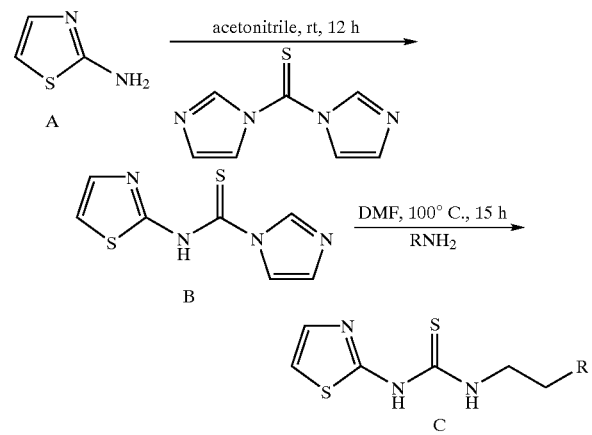

The thiazolyl thiourea compounds of the invention can be synthesized as described above, or by other known synthetic methods.

EXAMPLES

The invention may be further clarified by reference to the following Examples, which serve to exemplify the embodiments, and not to limit the invention in any way.

Example 1

Physicochemical Characteristics of Thiazolyl-thiourea Compounds

Proton and carbon nuclear magnetic resonance spectra were recorded on a Varian spectrometer using an automatic broadband probe. Unless otherwise noted, all NMR spectra were recorded in $CDCl_3$ at room temperature. The chemical shifts reported are in parts per million relative to tetramethyl silane as standard. The multiplicity of the signals were designated as follows: s, d, dd, t, q, m that corresponds to singlet, doublet, doublet of doublet, triplet, quartet and multiplet respectively. UV spectra were recorded using a Beckmann Model # DU 7400 UV/V is spectrometer with a cell path length of 1 cm. Fourier Transform Infra Red spectra were recorded using a FT-Nicolet model Protege #460 instrument. The infrared spectra of the liquid samples were run as neat liquids using KBr discs. Mass spectrum analysis was conducted using either a Finnigan MAT 95 instrument or a Hewlett-Packard Matrix Assisted Laser Desorption (MALDI) spectrometer model # G2025A. The matrix used in the latter case was cyano hydoxy cinnamic acid. Melting points were determined using a Melt John's apparatus and uncorrected. Atlantic Microlabs (Norcross, Ga.) performed the elemental analysis. Characterization data for the synthesized compounds is shown below:

N-[2-(2-Thiophenylethyl)]-N'-[2-(thiazolyl)]thiourea (Compound 1):

Yield 36%, mp 193–194° C.; UV (MeOH) $\lambda_{max}$ 207, 212, 215, 232, 236, 255, 289 nm; IR ν 3219, 3151, 3087, 3003, 2935, 1595, 1552, 1531, 1471, 1298, 1263, 1211, 1188, 1134, 1076, 846, 812, 686 $cm^{-1}$; $^1$HNMR (DMSO-$d_6$) δ 11.66 (br s, 1H), 9.69 (br s, 1H), 7.34 (d, 2H, J=3.3 Hz), 7.08 (d, 1H, J=3.6 Hz), 6.97–6.93 (m, 2H), 3.78 (q, 2H), 3.12 (t, 2H); $^{13}$C NMR (DMSO-$d_6$) δ 178.3, 161.9, 141.1, 136.5, 127.1, 125.6, 124.4, 112.1, 45.9, 28.6; MALDI-TOF 270.7 (M+1).

N-[2-(1-Cyclohexenylethyl)]-N'-[2-(thiazolyl)]thiourea (Compound 2):

Yield 38%, mp 153–154° C.; UV (MeOH) $\lambda_{max}$ 209, 258, 288 nm; IR ν 3170, 2993, 2922, 2833, 1565, 1514, 1489, 1379, 1307, 1257, 1238, 1180, 11330, 1093, 1084, 1059, 920, 829, 730, 707 $cm^{-1}$; $^1$H NMR (DMSO-$d_6$) δ 11.58 (br s, 1H), 9.69 (br s, 1H), 7.34 (d, 1H, J=3.6 Hz), 7.08 (d, 1H, J=3.6 Hz), 5.45 (s, 1H), 3.60 (q, 2H, J=5.7 Hz), 2.18 (t, 2H), 1.91 (d, 4H), 1.57–1.46 (m, 4H); $^{13}$C NMR (DMSO-$d_6$) δ 177.6, 161.7, 136.8, 134.3, 123.2, 112.2, 42.9, 36.5, 27.7, 25.0, 22.7, 22.2; MALDI-TOF 270.2 (M+2).

N-[2-(Phenoxyethyl)]-N'-[2-(thiazolyl)]thiourea (Compound 3):

Yield 48%, mp 168–169° C.; UV (MeOH) $\lambda_{max}$ 204, 259, 286 nm; IR ν 3610, 3556, 3180, 3039, 2935, 2875, 1566, 1511, 1460, 1284, 1248, 1184, 1112, 1082, 1053, 756, 690, 605 $cm^{-1}$; $^1$H NMR (DMSO-$d_6$) δ 11.70 (s, 1H), 9.88 (s, 1H), 7.39 (s, 1H), 7.31–7.26 (t, 2H, J=7.2 Hz), 7.11 (s, 1H), 6.98–6.91 (m, 3H), 4.16 (t, 2H), 3.93 (t, 2H); $^{13}$C NMR (DMSO-$d_6$) δ 160.7, 158.2, 129.6, 120.9, 114.6, 112.3, 65.6, 43.8; MALDI-TOF 280.8 (M+2).

N-[2-(4-Methylphenyl)ethyl]-N'-[2-(thiazolyl)]thiourea (Compound 4):

Yield 40%, mp 166–167° C.; UV (MeOH) $\lambda_{max}$ 208, 212, 259, 290 nm; IR ν 3170, 3047, 2997, 2943, 2920, 2850, 1562, 1514, 1449, 1348, 1323, 1279, 1217, 1196, 1159, 1097, 1053, 1020, 952, 868, 804, 760, 700 $cm^{-1}$; $^1$H NMR (DMSO-$d_6$) δ 11.58 (s, 1H), 9.66 (s, 1H), 7.34–7.32 (dd, 1H, J=3.9 Hz), 7.15–7.07 (q, 5H), 3.76–3.69 (q, 2H), 2.85–2.80 (t, 2H), 2.25 (s, 3H); $^{13}$C NMR (DMSO-$d_6$) δ 178.6, 162.4, 136.4, 135.9, 129.6, 129.2, 112.7, 46.6, 34.5, 31.5, 21.5; MS (MALDI-TOF) 279.3 (M+1).

N-[1-(1-Adamantyl)methyl]-N'-[2-(thiazolyl)]thiourea (Compound 5):

Yield 43%, mp 196–198° C.; UV (MeOH) $\lambda_{max}$ 204, 208, 259, 289 nm; IR ν 3166, 3041, 2898, 2844, 1569, 1510, 1197, 1180, 779, 744, 678 $cm^{-1}$; $^1$H NMR (DMSO-$d_6$) δ 10.96 (s, 1H), 10.66 (s, 1H), 7.34 (d, 1H, J=3.9 Hz), 6.84 (d, 1H, J=3.6 Hz), 6.84 (d, 2H, J=5.1 Hz), 2.18 (s, 3), 2.02 (s, 2H), 1.77–1.63 (m, 10H); $^{13}$C NMR (DMSO-$d_6$) δ 177.4, 161.9, 137.6, 110.9, 57.8, 40.5, 36.9, 33.9, 31.0, 28.3; MALDI-TOF 309 (M+2).

N-[1-(1-Furoylmethyl)]-N'-[2-(thiazolyl)]thiourea (Compound 6):

Yield 40%; mp 119–121° C.; UV (MeOH) $\lambda_{max}$ 204, 214, 257, 292 nm; IR ν 3170, 3071, 3030, 1565, 1509, 125, 1179 $cm^{-1}$; $^1$H NMR ($CDCl_3$) δ 11.10 (s, 2), 7.39 (q, 1H), 7.30 (d, 1H, J=3.6 Hz), 6.82 (d, 1H, J=3.9 Hz), 6.38–6.33 (m, 2H), 4.93 (d, 2H); $^{13}$C NMR ($CDCl_3$) δ 177.8, 161.9, 150.1, 142.6, 137.9, 111.6, 110.7, 108.5, 42.65; MALDI-TOF 241.9.

N-[3-(2-Imidazole)propyl]-N'-[2-(thiazolyl)]thiourea (Compound 7):

Yield 44%; mp 176–177° C.; UV (MeOH) $\lambda_{max}$ 213, 258, 289 nm; IR ν 3190, 3051, 2932, 1565, 1514, 1225 $cm^{-1}$; $^1$H NMR (DMSO-$d_6$) δ 11.39(s, 1H), 9.98 (s, 1H), 7.53 (s, 1H), 7.25 (d, 1H, J=3.9 Hz), 7.02 (s, 1H), 6.88 (s, 1H), 6.85 (d, 1H, J=3.6 Hz), 3.54 (q, 2H), 3.01 (t, 2H), 2.12–2.03 (m, 2H); $^{13}$C NMR (DMSO-$d_6$) δ 178.9, 162.4, 137.5, 137.3, 129.2, 119.5, 111.9, 102.8, 44.6, 30.5; MALDI-TOF 269.7.

N-[2-(2-Indole)ethyl]-N'-[2-(thiazolyl)]thiourea (Compound 8):

Yield 51%; mp 212–213° C.; UV (MeOH) $\lambda_{max}$ 204, 207, 221, 285 nm; IR ν 3386, 3164, 3076, 3035, 1560, 1514, 1184, 750 $cm^{-1}$; $^1$H NMR (DMSO-$d_6$) δ 11.56 (s, 1H), 10.86 (s, 1H), 9.73 (s, 1H), 7.62 (d, 1H, J=7.5 Hz), 7.35 (s, 1H), 7.31 (t, 1H), 7.20 (s, 1H), 7.07 (d, 1H, J=6.9 Hz), 7.03 (s, 1H), 6.96 (t, 1H), 3.81 (q, 2H), 3.00 (t, 2H); $^{13}$C NMR (DMSO-$d_6$) δ 178.4, 162.3, 136.9, 127.7, 123.8, 121.7, 119.1, 118.9, 112.7, 112.1, 111.8, 102.8, 45.9, 24.9; MALDI-TOF 304.2.

N-[2-(2-Piperdine)ethyl]-N'-[2-(thiazolyl)]thiourea (Compound 9):

Yield 50%; mp 163–164° C.; UV (MeOH) $\lambda_{max}$ 204, 207, 211, 258, 290 nm; IR ν 3169, 3019, 2931, 1556, 1512, 1181 $cm^{-1}$; $^1$H NMR (DMSO-$d_6$) δ 10.75 (s, 2H), 7.33 (d, 1H, J=3.3 Hz), 6.82 (d, 1H, J=3.6 Hz), 3.78 (t, 2H), 2.59 (t, 2H), 2.45 (s, 5H), 1.60 (t, 3H), 1.45 (d, 3H); $^{13}$C NMR (DMSO-$d_6$) δ 177.1, 161.9, 137.8, 111.4, 107.5, 56.4, 54.5, 43.2, 26.5, 24.8; MALDI-TOF 272.1.

N-[2-(4-Hydroxyphenyl)ethyl]-N'-[2-(thiazolyl)]thiourea (Compound 10):

Yield 47%; mp 160–161° C.; UV (MeOH) $\lambda_{max}$ 209, 219, 225, 260, 289 nm; IR ν 3437, 3050, 1581, 1556, 1518 $cm^{-1}$; $^1$H NMR (DMSO-$d_6$) δ 11.57 (s, 1H), 9.66 (s, 1H), 9.22 (s, 1H), 7.33 (d, 1H, J=3.6 Hz), 7.06 (t, 3H), 6.68 (d, 2H, J=8.11 Hz), 3.68 (q, 2H), 2.76 (t, 2H); $^{13}$C NMR (DMSO-$d_6$) δ 178.5, 162.3, 156.4, 137.3, 130.3, 129.5, 115.9, 112.7, 46.9, 34.1; MALDI-TOF 280.6.

N-[2-Pyridylethyl]-N'-[2-(thiazolyl)]thiourea (Compound 11):

Yield 60%; mp 140–141° C.; UV (MeOH) $\lambda_{max}$ 209, 262, 269, 288 nm; IR v 3176, 3047, 3002, 2937, 1581, 1558, 1514, 1475, 1433, 1342, 1304, 1246, 1167, 1147, 1068, 1020, 989, 869, 789, 752, 690 $cm^{-1}$; $^1$H NMR (DMSO-$d_6$) δ 11.59 (bs, 1), 9.77(bs, 1H), 8.51–8.49 (d, 1H), 7.72–7.67 (m, 1H), 7.31–7.26 (m, 2H), 7.23–7.19 (m, 1H), 7.06–7.05 (m, 1H), 3.95–3.89 (m, 2H), 3.07–3.02 (m, 2H); $^{13}$C NMR (DMSO-$d_6$) δ 178.1, 161.8, 158.7, 149.2, 136.7, 129.4, 123.5, 121.8, 112.2, 43.9, 36.2; MALDI-TOF: 266.3 (M+2).

N-[3-(Pyrrolidinone)propyl]-N'-[2-(thiazolyl)]thiourea (Compound 12):

Yield 56%; mp 123.5–126° C.; UV (MeOH) $\lambda_{max}$ 205, 256, 290 nm; IR v 3199, 3054, 2964, 2863, 1660, 1550, 1508, 1315, 1166, 699 $cm^{-1}$; $^1$H NMR (DMSO-$d_6$) δ 11.61 (s, 1H), 9.56 (s, 1H), 7.37 (d, 1H, J=3.6 Hz), 7.08 (d, 1H, J=3.6 Hz), 3.48 (q, 2H), 3.21 (t, 4H), 2.19 (t, 2H), 1.90 (t, 2H), 1.75 (t, 2H); $^{13}$C NMR (DMSO-$d_6$) δ 173.9, 161.9, 136.4, 122.8, 112.0, 102.7, 46.4, 41.9, 30.7, 26.3, 17.8; MALDI-TOF: 282.6.

N-[α-Ethylbenzyl]-N'-[2-(thiazolyl)]thiourea (Compound 13):

Yield 44%; mp 149–151° C.; UV (MeOH) $\lambda_{max}$ 210, 258, 291 nm; IR v 3166, 3022, 2931, 1576, 1511, 1189, 1054, 698 $cm^{-1}$; $^1$H NMR (CDCl$_3$) δ 11.18 (s, 2H), 7.36–7.31 (m, 6H), 6.80 (d, 1H, J=3.6 Hz), 5.52–5.45 (m, 1H), 2.10–1.92 (m, 2H), 0.97 (t, 3H); $^{13}$C NMR(CDCl$_3$) δ 177.0, 162.3, 141.3, 137.8, 128.8, 127.5, 111.5, 61.0, 29.9, 10.9; MALDI-TOF: 279.5.

Example 2

Comparison of Thiazolyl Thiourea Compounds with Other NNRTI

Using the method described in Uckun et. al., 1998, *Antimicrobial Agents and Chemotherapy* 42:383, the anti-HIV activity of compounds 1–13 was measured by determining their ability to inhibit the replication of HIV-1 strain HTLV$_{IIIB}$ in human peripheral blood mononuclear cells (PBMC) from healthy individuals. The same method was used to measure the activity of compounds 1 to 8 and compound 13 against NNRTI-resistant HIV-1 strains A17 with a Y181C mutation in RT and A17 variant with a Y181C plus K103N mutations in RT. Data are shown in Table 1.

Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2, 2 mM L-glutamine, 25 mM HEPES, 2 g/L NaHCO$_3$, 50 μg/mL gentamicin, and 4 μg/mL phytohemagglutinin prior to exposure to the HIV-1 strain HTLV$_{IIIB}$. The cells were then infected with virus at a multiplicity of infection (MOI) of 0.1 during a 1-hour adsorption period at 37° C. in a humidified 5% CO$_2$ atm. Subsequently, cells were cultured in 96-well microtiter plates (100 μl/well; 2×10$^6$ cells/mL) in the presence of various inhibitor concentrations. Aliquots of culture supernatants were removed from the wells on the 7th day after infection for p24 antigen assays. The applied p24 enzyme immunoassay (EIA) was the unmodified kinetic assay commercially available from Coulter Corporation/Immunotech, Inc. (Westbrooke, Me.), which utilizes a murine mAb to HIV core protein coated onto microwell strips to which the antigen present in the test culture supernatant samples binds. Percent viral inhibition was calculated by comparing the p24 values from the test substance-treated infected cells with p24 values from untreated infected cells (i.e., virus controls). The effects of various treatments on cell viability were also examined and the results were expressed as the cytotoxic concentration (CC)$_{50}$ values. The selectivity indices (SI) were calculated using the formula: SI=CC$_{50}$/IC$_{50}$.

TABLE 1

Anti-HIV activity of thiazolyl thiourea compounds.

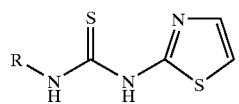

1-13

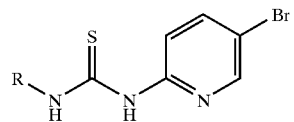

HI-244 and HI-443

| Compound | R | Potency and Selectivity | | | Activity Against NNRTI-resistant HIV | |
| --- | --- | --- | --- | --- | --- | --- |
| | | IC$_{50}$ HTLV$_{HIB}$(μM) | CC$_{50}$ (μM) | SI | IC$_{50}$(μM) A17 | A17 variant |
| 1 | | <0.001 | 71 | 71,000 | >100 | N.D. |

TABLE 1-continued
Anti-HIV activity of thiazolyl thiourea compounds.
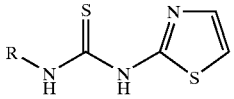
1-13
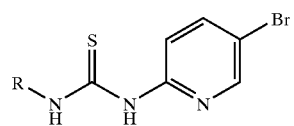
HI-244 and HI-443
| | | Potency and Selectivity | | | Activity Against NNRTI-resistant HIV | |
|---|---|---|---|---|---|---|
| | | IC$_{50}$ | CC$_{50}$ | | IC$_{50}$ ($\mu$M) | |
| Compound | R | HTLV$_{IIIB}$ ($\mu$M) | ($\mu$M) | SI | A17 | A17 variant |
| 2 | 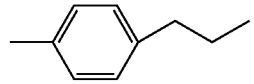 | 0.007 | 4 | 571 | 0.9 | >100 |
| 3 | 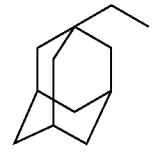 | <0.001 | >100 | >100,000 | 4.4 | >100 |
| 4 | 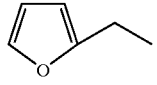 | 0.07 | >100 | 1429 | 3.9 | >100 |
| 5 | 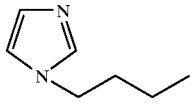 | <0.001 | 40 | 40,000 | 0.6 | 1.3 |
| 6 | 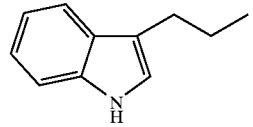 | <0.001 | >100 | >100,000 | 2.0 | 0.6 |
| 7 | 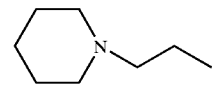 | <0.001 | 35 | 35,000 | >100 | >100 |
| 8 | 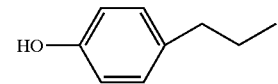 | <0.001 | 28 | 28,000 | 2.2 | 3.7 |
| 9 | 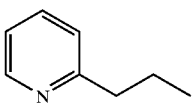 | >100 | N.D | N.D | N.D. | N.D. |
| 10 |  | >100 | N.D. | N.D. | N.D. | N.D. |
| 11 |  | 1 | 100 | 100 | N.D. | N.D. |

TABLE 1-continued

Anti-HIV activity of thiazolyl thiourea compounds.

[Structures shown: General thiazolyl thiourea structure (compounds 1-13) and bromopyridyl thiourea structure (HI-244 and HI-443)]

| Compound | R | Potency and Selectivity IC$_{50}$ HTLV$_{IIIB}$(μM) | CC$_{50}$ (μM) | SI | Activity Against NNRTI-resistant HIV IC$_{50}$(μM) A17 | A17 variant |
|---|---|---|---|---|---|---|
| 12 | [pyrrolidinone-butyl group] | 9 | 18 | 2 | N.D. | N.D. |
| 13 | [1-phenylethyl/sec-butylbenzene group] | 0.009 | 10 | 1111 | 2.1 | 1.5 |
| Nevirapine | N.A. | 0.034 | N.D. | N.D. | >100 | >100 |
| Delavirdine | N.A. | 0.009 | N.D. | N.D. | 50 | >100 |
| HI-443 | [thiophene-propyl group] | 0.030 | >100 | N.D. | 0.048 | 3.3 |
| HI-244 | [H$_3$C-phenyl-propyl group] | 0.007 | >100 | N.D. | 0.070 | >100 |

Six lead compounds inhibit HIV-1 replication with sub-nanomolar IC$_{50}$ values: N-[2-(2-Thiophenylethyl)]-N'-[2-(thiazolyl)]thiourea (Compound 1), N-[2-(Phenoxyethyl)]-N'-[2-(thiazolyl)]thiourea (Compound 3), N-[1-(1-Adamantyl)methyl]-N'-[2-(thiazolyl)]thiourea (Compound 5), N-[1-(1-Furoylmethyl)]-N'-[2-(thiazolyl)]thiourea (Compound 6), N-[3-(2-Imidazole)propyl]-N'-[2-(thiazolyl)]thiourea (Compound 7), and N-[2-(2-Indole)ethyl]-N'-[2-(thiazolyl)]thiourea (Compound 8). These six lead compounds are minimally toxic to PBMC with CC$_{50}$ values ranging from 28 μM to >100 μM and their selectivity indices are remarkably high ranging from 28,000 to >100,000. The 6 lead compounds are between 9 and 34 times more potent than the standard NNRTI nevirapine and delavirdine and between 7 and 30 times more potent than the previously reported NNRTI HI-443 and HI-244.

Compounds 2–6, 8, and 13 inhibit A17 at nanomolar concentrations with IC$_{50}$ values ranging from 0.6 μM to 4.4 μM, which are approximately 1-log better than the IC$_{50}$ values of HI-443 or RT-244 and 1–2 logs better than the IC$_{50}$ values of nevirapine or delavirdine against the same NNRTI-resistant HIV-1 strain. Additionally, compounds 5, 6, 8, and 13 are very effective against A17 variant with IC$_{50}$ values ranging from 0.6 μM to 3.7 μM, which are similar to the IC$_{50}$ value of HI-443 and almost 2-logs better than the IC$_{50}$ values of nevirapine, delavirdine, or compound HT-244 against the same NNRTI-resistant HIV-1 strain.

Compounds 5, 6, 8, and 13 were effective against both NNRTI-resistant HIV-1 isolates at nanomolar to low micromolar concentrations and exhibit much greater potency against both wild-type as well as NNRTI-resistant HIV-1 than nevirapine, delavirdine, HI-443, and HI-244. Compound 6 is particularly promising because it was minimally toxic to PBMC and had a selectivity index of >100,000.

Example 3

X-Ray Crystal Structures

Figure 1B:
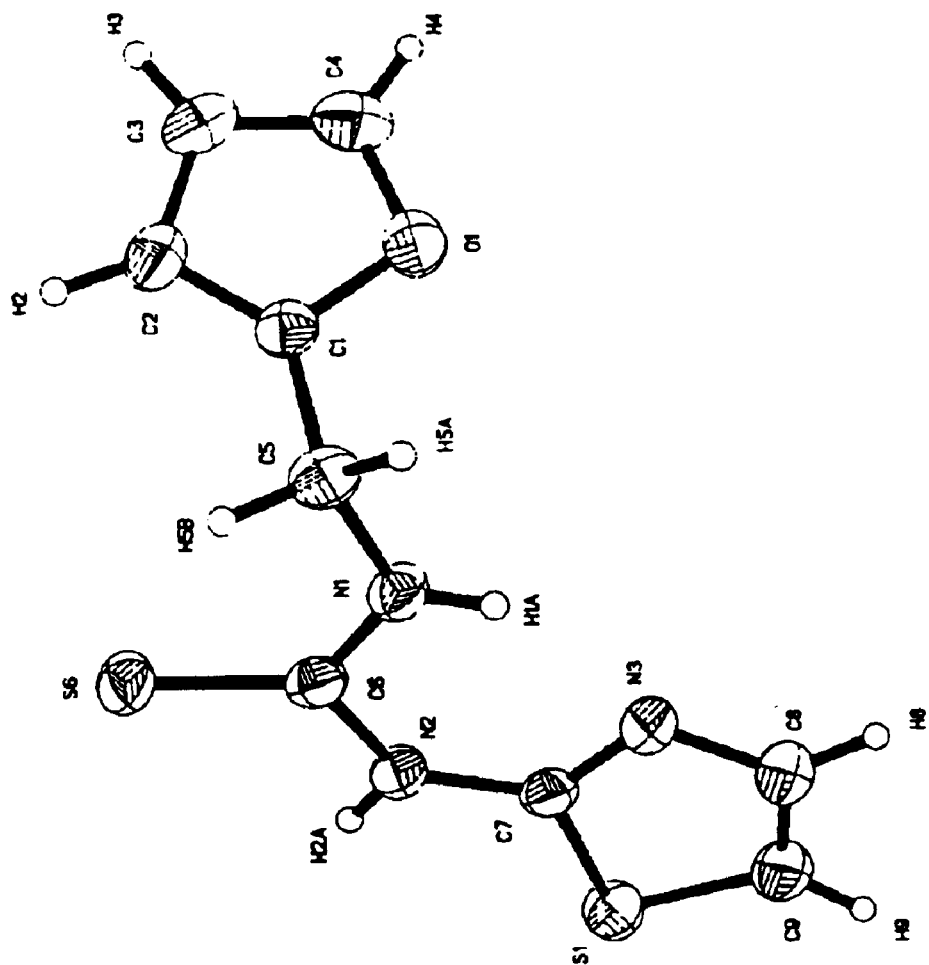
Figure 1C:
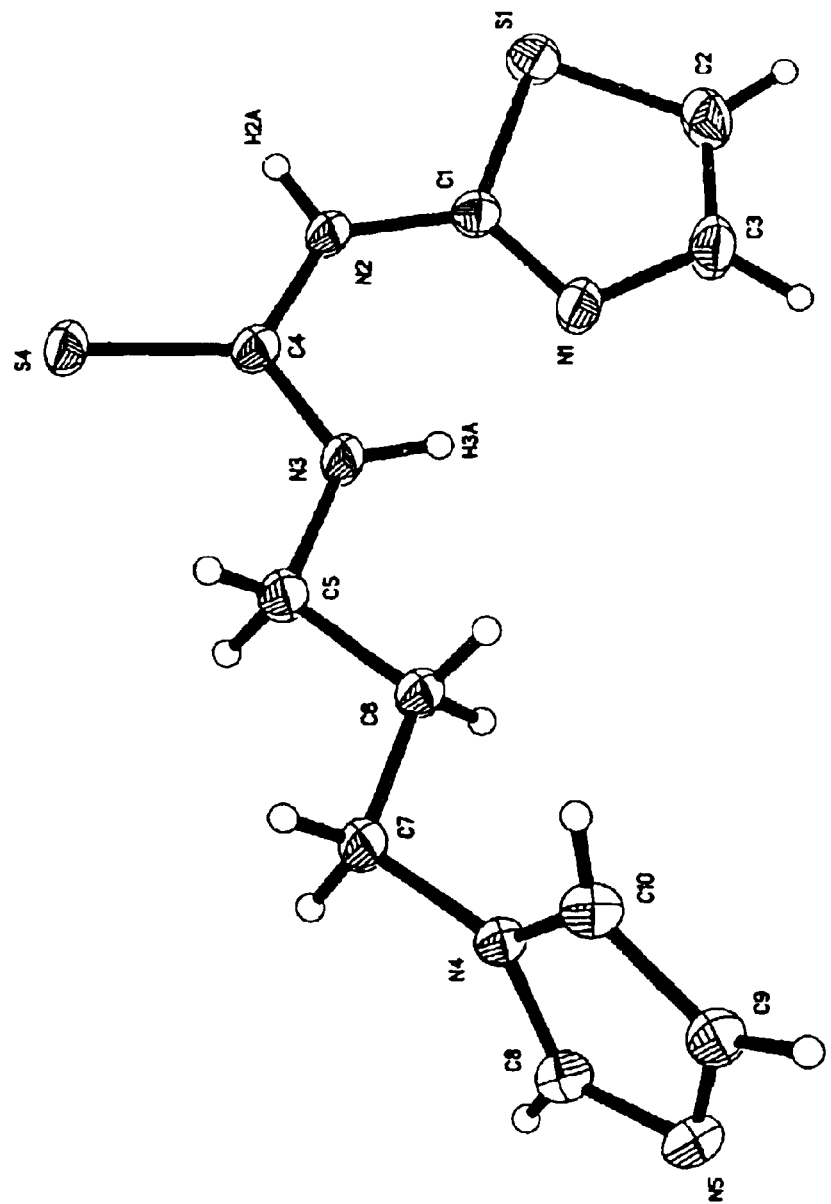
Figure 1D:
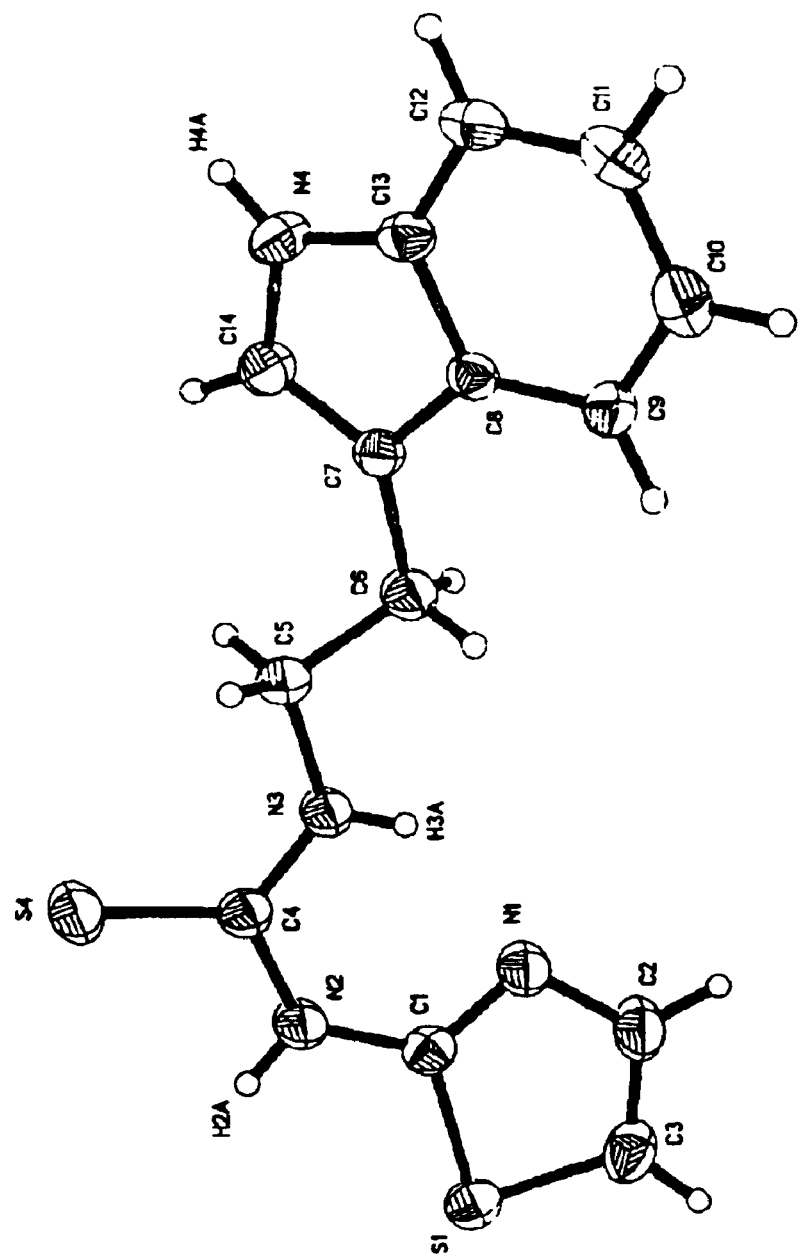

The structures of compounds 2 and 6–8 were resolved by X-ray crystallography and are diagramatically shown in FIGS. 1A–1D. The X-ray structures confirmed that the essential binding components for the NNRTI binding pocket are present in these new compounds. For example, the crystal structures of compounds 2 and 6–8 show that each molecule contains an intramolecular hydrogen bond between a thiourea NH and a nitrogen atom on the thiazolyl ring. The more compact molecular conformation resulting from this hydrogen bond allows the molecule to more easily fit into the nonucleoside-binding site of HIV RT and is consistent with molecular modeling studies evaluating how NNRTI compounds can bind to HIV RT. These molecular modeling studies are preveiously described in WO99/47501 and U.S. Pat. No. 5,998,411.

The crystal structures of these four compounds and molecular studies indicate that conformations of these thiazolyl thiourea compounds could be adjusted (using a different rotamer conformation) to fit the binding pocket. The individual interactions between the compound and the binding pocket determine the binding affinity.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound:

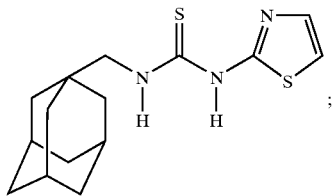

or a pharmaceutically acceptable salt thereof.

2. A pharmaceutical composition comprising a therapeutically effective amount of a compound of claim 1 and a pharmaceutically acceptable carrier or diluent.

3. A method for treating HIV infection in a subject by inhibiting HIV reverse transcriptase comprising administering to said subject an effective amount of a compound of claim 1.

4. A method for treating NNRTI resistant HIV in a subject comprising administering to said subject an effective amount of a compound of claim 1.

5. A method for treating multi-drug resistant HIV in a subject comprising administering to said subject an effective amount of a compound of claim 1.

6. A method for treating NNRTI resistant HIV in a subject comprising administering to said subject an effective amount of a compound of the formula:

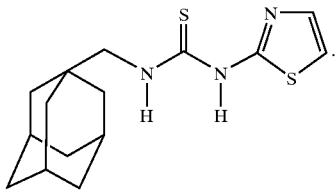

7. A method for treating multi-drug resistant HIV in a subject comprising administering to said subject an effective amount of a compound of the formula:

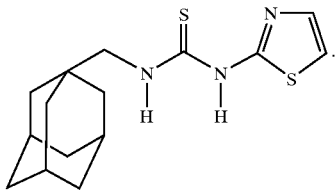

* * * * *

UNITED STATES PATENT AND TRADEMARK OFFICE
CERTIFICATE OF CORRECTION

PATENT NO.        : 6,960,606 B2                                      Page 1 of 1
APPLICATION NO.   : 10/420031
DATED             : November 1, 2005
INVENTOR(S)       : Uckun et al.

It is certified that error appears in the above-identified patent and that said Letters Patent is hereby corrected as shown below:

Col. 1, line 50: "resistant to NNTI compounds," should read --resistant to NNRTI compounds,--

Col. 3, line 63: "inhibitors of MV reverse" should read --inhibitors of HIV reverse--

Col. 4, line 49: "rings, Such as" should read: --rings, such as--

Col. 6, line 14: "where W is unsubstituted" should read --where $R^3$ is unsubstitued--

Col. 9, line 39: "$^1$HNMR (DMSO-$d_6$)" should read -- $^1$H NMR (DMSO-$d_6$)

Col. 15, line 61: "values of HI-443 or RT-244" should read --values of HI-443 or HI-244--

Col. 15, line 66: "or compound HT-244" should read --or compound HI-244--

Signed and Sealed this

Twenty-second Day of August, 2006

JON W. DUDAS
*Director of the United States Patent and Trademark Office*